United States Patent [19]

Ryang

[11] Patent Number: 4,472,565
[45] Date of Patent: Sep. 18, 1984

[54] SILICONE-POLYIMIDE COPOLYMERS, CONDENSATION VULCANIZABLE COMPOSITIONS OBTAINED THEREFROM, AND METHODS FOR MAKING

[75] Inventor: Hong-Son Ryang, Camarillo, Calif.

[73] Assignee: General Electric Company, Schenectady, N.Y.

[21] Appl. No.: 567,609

[22] Filed: Jan. 3, 1984

Related U.S. Application Data

[63] Continuation-in-part of Ser. No. 442,682, Nov. 18, 1982, abandoned.

[51] Int. Cl.$^3$ .............................................. C08G 77/04
[52] U.S. Cl. ..................................... 528/26; 525/431; 525/474; 525/478; 528/31; 556/407; 556/419
[58] Field of Search ................... 528/26, 31; 525/474, 525/478, 431; 556/419, 407

[56] References Cited

U.S. PATENT DOCUMENTS

| | | | |
|---|---|---|---|
| 3,288,754 | 11/1966 | Green | 528/26 |
| 3,325,450 | 6/1967 | Holub | 528/26 |
| 3,338,859 | 8/1967 | Green | 528/26 |
| 4,381,396 | 4/1983 | Ryang | 549/237 |
| 4,404,350 | 9/1983 | Ryang | 525/431 |

OTHER PUBLICATIONS

Effect of Elastomer Chain Length on Silicon-Modified Polyimide Properties, Ezzell et al., Abstract of 33rd Southern Regional ACS Mtg. p. 107, (1981).

Moshinskii et al, Chemical Abstracts, vol. 72, (1970).
Derwent, Week D38, p. 17, Soviet Union 761,251, 4/9/78.
Siloxanmodifizierte Polypyromellitimide, Kuckertz, Die Makromolekulare Chemie, 98 (1966) 101–108.
Polyimides from Silicon–Containing Dianhyrides and Diamines, Johnston et al., ACS Org. Cont. Plast. Chem. V 33, 1973, pp. 169–176.
Organosilicon Compounds, XVIII, Silicon–Containing Dianhydrides, Pratt et al., J. Org. Chem., vol. 38, No. 25, 1973, pp. 4271–4274.
Nishizaki et al. Chem. Abstracts, vol. 63, 1965, 3057b.

*Primary Examiner*—Melvyn I. Marquis
*Attorney, Agent, or Firm*—William A. Teoli; James C. Davis, Jr.; James Magee, Jr.

[57] ABSTRACT

Silicone-polyimide copolymers having terminal silanol or silicon hydride radicals are provided based on the use of a norbornene terminated polyimide. A hydrosilation reaction is employed to introduce silicon-hydrogen into the terminal position of the polyimide having norbornene termination. The resulting hydrosilyl terminated polyimide is reacted with silanol terminated polydiorganosiloxane in the presence of a catalyst to produce silanol terminated polydiorganosiloxane-polyimide copolymer. Room temperature or low temperature condensation vulcanizable compositions based on the use of such silanol-terminated copolymers provide cured silicon-polyimide copolymers exhibiting improved toughness.

13 Claims, No Drawings

SILICONE-POLYIMIDE COPOLYMERS, CONDENSATION VULCANIZABLE COMPOSITIONS OBTAINED THEREFROM, AND METHODS FOR MAKING

CROSS REFERENCE TO RELATED APPLICATIONS

This application is a continuation-in-part application of Ser. No. 442,682, filed Nov. 18, 1982, now abandoned, and assigned to the same assignee as the present invention. Reference is made to my copending application Ser. No. 395,932, filed July 7, 1982, now U.S. Pat. No. 4,381,396, for Silylnorbornane Anhydrides and Method for Making and Ser. No. 935,933, filed July 7, 1982, now U.S. Pat. No. 4,404,350, for Silicon-imide Copolymers and Method for Making, both applications being assigned to the same assignee as the present invention.

BACKGROUND OF THE INVENTION

The present invention relates to silanol terminated polydiorganosiloxane-polyimide copolymers, or silicon hydride terminated polydiorganosiloxane-polyimide copolymers and room temperature, or low temperature condensation vulcanizable compositions obtained therefrom and methods for making such materials. More particularly, the present invention relates to the hydrosilation of norbornene terminated polyimides and the subsequent reaction of the resulting silicon-hydrogen terminated polyimides with silanol terminated polydiorganosiloxane.

Prior to the present invention, room temperature vulcanizable silanol terminated polydiorganosiloxanes, for example, silanol terminated polydimethylsiloxanes were available in either one-package or two-package systems based on the nature of the moisture sensitive cross-linking agents utilized in the composition. A typical one-package system is based on the use of methyltriacetoxysilane and a silanol terminated polydimethylsiloxane as shown by Ceyzeriat, U.S. Pat. No. 3,133,891. A two-package system as shown by Nitzsche et al, U.S. Pat. No. 3,065,194 requires the blending of silanol terminated polydimethylsiloxane with a curing catalyst, such as ethyl orthosilicate in combination with dibutyltindilaurate. The two-package system requires mixing of the curing catalyst with the silanol terminated polydimethylsiloxane prior to use.

The above described one-package and two-package room temperature vulcanizable compositions generally require the use of reinforcing filler, for example, a silica filler in amounts of from 5-300 parts, per 100 parts of silicone polymer, if improved tensile strength to the resulting cured silicone is desired. Another procedure available to improve the toughness of the cured silicone polymers is the introduction of silarylenesiloxy units into the polymer chain to produce a copolymer consisting essentially of diorganosiloxy units chemically combined with silarylenesiloxy units. Although these procedures substantially enhance the modulus (psi) of the silicone polymer, these procedures are uneconomic or do not achieve the degree of physical properties desired in the end product.

The present invention is based on the discovery that room temperature or low temperature condensation vulcanizable polydiorganosiloxane-polyimide copolymers have been found to provide elastomers exhibiting tensile strength in the range of 100 psi to 10,000 psi when cured with conventional room temperature vulcanizable curing catalysts. These silanol terminated or silicon hydride terminated polydiorganosiloxane-polyimide copolymers comprise by weight from 1 to 99% of polyimide blocks of the formula,

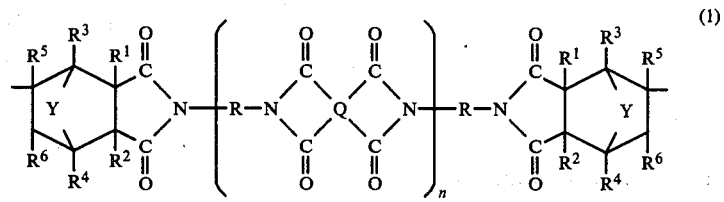

chemically combined with from 99% to 1% of polydiorganosiloxane blocks of the formula,

where R is a divalent radical selected from the class consisting of (a) aromatic hydrocarbon radicals having from 6–20 carbon atoms and halogenated aromatic hydrocarbon radicals having from 6–20 carbon atoms, (b) alkylene radicals having from 2–20 carbon atoms and cycloalkylene radicals having from 2–20 carbon atoms, (c) $C_{(2-8)}$ alkylene terminated polydiorganosiloxane, and (d) radicals included by the general formula,

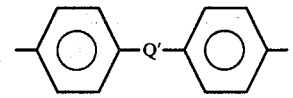

Q' is a member selected from the class consisting of

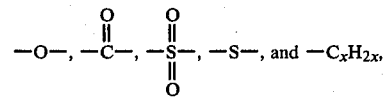

x is a whole number from 1 to 5 inclusive, Q is a tetravalent radical selected from

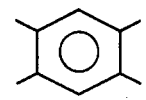

and

-continued

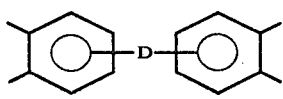

where D is a member selected from

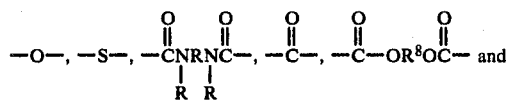

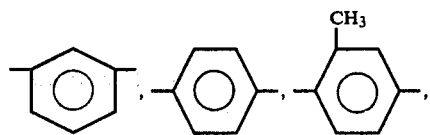

and $R^8$ is a divalent radical selected from

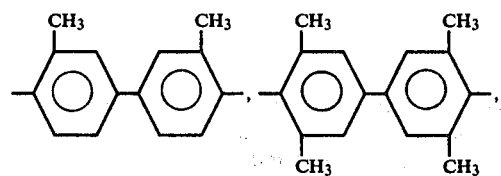

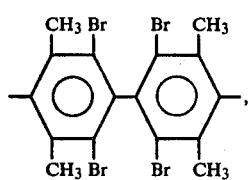

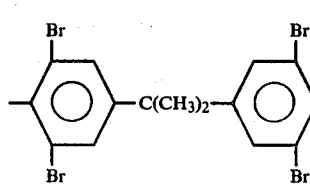

and divalent organic radicals of the general formula,

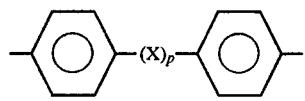

X is a member selected from the class consisting of divalent radicals of the formula,

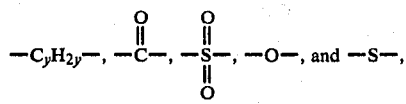

y is an integer from 1 to 5, $R^1$–$R^6$ are selected from hydrogen and $C_{(1-8)}$ alkyl radicals, $R^7$ is the same or different $C_{(1-13)}$ monovalent hydrocarbon radical and substituted $C_{(1-13)}$ monovalent hydrocarbon radical, Y is a divalent radical selected from —O— and —C($R^1$)$_2$—, n is an integer equal to 0–200 inclusive, m is an integer equal to 1–2000 inclusive and p is equal to 0 or 1.

The silicon hydride terminated polydiorganosiloxane-polyimide copolymers of the present invention can be made by initially forming a norbornene terminated polyimide by effecting reaction between organic diamine, a norbornene anhydride and organic dianhydride, in accordance with the following equation:

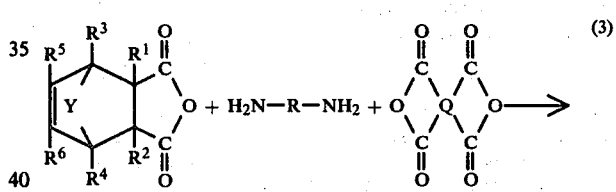

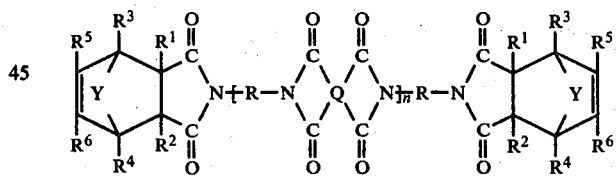

where Q, R, $R^1$–$R^6$, n and Y are as previously defined.

The aliphatically unsaturated polyimide of formula (3) is thereafter hydrosilated with a silicon hydride having the formula,

where r is 0 or 1, $R^9$ is selected from hydrogen and $R^7$, to produce silicon hydride terminated polyimide having the formula,

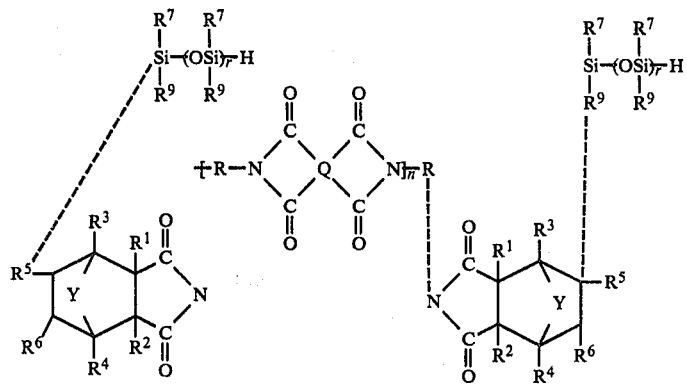
(5)

where R–R⁷, Y, Q and n are as previously defined.

The silanol terminated polydiorganosiloxane polyimide copolymers of the present invention have the formula,

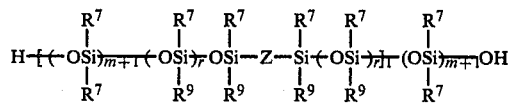
(6)

where Z is a divalent group shown by formula (1), can be prepared by effecting reaction between the silicon hydride terminated polyimide of formula (5) and a silanol terminated polydiorganosiloxane of the formula,

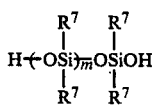
(7)

in the presence of an effective amount of condensation catalyst as defined hereinafter, where $R^7$, $R^9$ r and m are as previously defined and l is an integer having a value of from about 1 to $10^4$ inclusive.

Radicals included within $R^1$–$R^6$ of formulas 1, 3 and 4 are, for example, hydrogen, methyl, ethyl, propyl, butyl, etc. Radicals included within $R^7$ are, for example, aryl radicals and halogenated aryl radicals, for example, phenyl, chlorophenyl, tolyl, xylyl, biphenyl, naphthyl, etc.; alkenyl radicals, for example, vinyl, allyl, cyclohexenyl, etc.; $C_{(1-8)}$ alkyl radicals and halogenated alkyl, for example, methyl, ethyl, propyl, butyl, octyl, etc.

STATEMENT OF THE INVENTION

There is provided by the present invention condensation vulcanizable compositions comprising by weight
(A) 100 parts of a silanol terminated polydiorganosiloxane-polyimide copolymer of formulas (6),
(B) 0.002 to 10 parts of a curing agent,
(C) 0 to 5 parts of a condensation catalyst and
(D) 0 to 3000 parts of a silanol-terminated polydiorganosiloxane of formula (7).

Curing agents which can be utilized in the practice of the present invention in the above-described condensation vulcanizable compositions are, for example, methyltriacetoxysilane, methyl-tris-(2-ethylhexanoxy)silane, and a curing agent having the formula

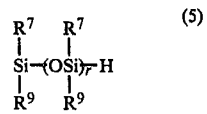

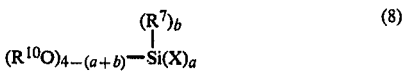
(8)

where $R^7$ is as previously defined, $R^{10}$ is a $C_{(1-8)}$ aliphatic organic radical selected from the group consisting of alkyl, alkylether, alkylester, alkylketone, and alkylcyano radicals, or $C_{(7-13)}$ aralkyl radical, X is a hydrolyzable leaving group selected from the group consisting of acyloxy, amido, amino, carbamato, enoxy, halo, imidato, isocyanato, ketoximato, oximato, thioisocyanato and ureido radicals and b is a whole number equal to 0 or 1, a is a whole number equal to 0 to 4 inclusive and the sum of a+b is equal to 0 to 4 inclusive.

In addition to curing agents of formula (8), there also can be utilized in the condensation vulcanizable compositions of the present invention alkoxy functional crosslinking agents of the formula

(9)

where $R^7$, $R^{10}$ and b are as previously defined.

Condensation catalysts can be used in the practice of the present invention to facilitate the cure of the condensation vulcanizable compositions and in certain cases facilitate the condensation of the silanol terminated polydiorganosiloxane of formula (6) with the silicon hydride terminated polyimide of formula (5). For example, there can be used from 0.001 to 1 part of condensation catalyst, based on 100 parts of the above described silanol terminated polydiorganosiloxane-polyimide copolymer. There are included as condensation catalysts tin compounds, for example, dibutyltindilaurate; dibutyltindiacetate; dibutyltindimethoxide; carbomethoxyphenyl tin tris-uberate; tin octoate; isobutyl tin triceroate; dimethyl tin dibutyrate; dimethyl tin dineodeconate; triethyl tin tartrate; dibutyl tin dibenzoate; tin oleate; tin naphthenate; butyltin-tri-2-ethylhexoate; tinbutyrate. The preferred condensation catalysts are tin compounds and dibutyltindiacetate is particularly preferred.

Titanium compounds which can be used are, for example, 1,3-propanedioxytitanium bis(ethylacetoacetate); 1,3-propanedioxytitanium bis(acetylacetonate); diisopropoxytitanium bis(acetylacetonate); titanium naphthenate; tetrabutyltritanate; tetra-2-ethylhexyltitanate; tetraphenyltitanate; tetraoctadecyltitanate; ethyltriethanolaminetitanate. In addition, beta-dicarbonyltitanium compounds as shown by Weyenberg U.S. Pat. No. 3,334,067 can be used as condensation catalysts in the present invention.

Zirconium compounds, for example, zirconium octoate, also can be used.

Further examples of metal condensation catalysts are, for example, lead 2-ethyloctoate; iron 2-ethylhexoate; cobalt 2-ethylhexoate; manganese 2-ethylhexoate; zinc 2-ethylhexoate; antimony octoate; bismuth naphthenate; zinc naphthenate; zinc stearate.

Examples of nonmetal condensation catalysts are hexylammonium acetate and benzyltrimethylammonium acetate.

In addition to the above described one-package condensation vulcanizable curing agents, there also can be used in the practice of the present invention, curing agents which can be added to the silanol terminated polydiorganosiloxane-polyimide copolymer to provide two-package condensation vulcanizable compositions as shown by Nitzsche et al, U.S. Pat. No. 3,127,363, incorporated herein by reference.

Some of the organic dianhydrides which can be used in the practice of the present invention to produce the norbornene terminated polyamide of formula (3) along with norbornene anhydride chain-terminating monomers are, for example, benzophenone dianhydride, pyromellitic dianhydride, 2,2-bis[4-(3,4-dicarboxyphenoxy)phenyl]propane dianhydride, 2,2-bis[4-(2,3-dicarboxyphenoxy)phenyl]propane dianhydride, 4-(2,3-dicarboxyphenoxy)-4'-(3,4-dicarboxyphenoxy)diphenyl-2,2-propane dianhydride, and bisnorbornanesiloxane dianhydride of the formula,

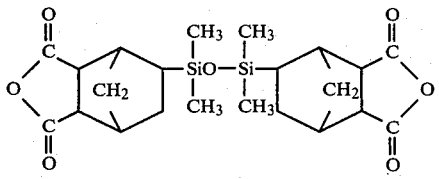

and mixtures thereof.

Organic diamines which can be used to make the polyimide blocks of the silanol terminated polydiorganosiloxane-polyimide copolymers are, for example,
o-phenylenediamine;
m-phenylenediamine;
p-phenylenediamine;
4,4'-diaminodiphenylpropane;
4,4'-diaminodiphenylmethane (commonly named 4,4'-methylenedianiline);
4,4'-diaminodiphenyl sulfide (commonly named 4,4'-thiodianiline);
4,4'-diaminodiphenyl ether (commonly named 4,4'-oxydianiline);
1,5-diaminonaphthalene;
3,3'-dimethylbenzidine;
3,3'-dimethoxybenzidine;
2,4-bis($\beta$-amino-t-butyl)toluene;
1,3-diamino-4-isopropylbenzene;
1,2-bis(3-aminopropoxy)ethane;
benzidine;
m-xylylenediamine;
p-xylylenediamine,
2,4-diaminotoluene;
2,6-diaminotoluene;
bis(4-aminocyclohexyl)methane;
3-methylheptamethylenediamine;
4,4-dimethylheptamethylenediamine;
2,11-dodecanediamine;
2,2-dimethylpropylenediamine;
octamethylenediamine;
3-methoxyhexamethylenediamine;
2,5-dimethylhexamethylenediamine;
2,5-dimethylheptamethylenediamine;
3-methylheptamethylenediamine;
5-methylnonamethylenediamine;
1,4-cyclohexanediamine;
1,12-octadecanediamine;
bis(3-aminopropyl)sulfide;
N-methyl-bis(3-aminopropyl)amine;
hexamethylenediamine;
heptamethylenediamine;
nonamethylenediamine;
decamethylenediamine;
bis(3-aminopropyl)tetramethyldisiloxane;
bis(4-aminobutyl)tetramethyldisiloxane,
and mixtures of such diamines.

Some of the silicon hydrides of formula (4) which can be employed in the practice of the present invention to introduce silicon hydride functional groups into the polyimide having aliphatically unsaturated norbornene groups are, for example, diorganosiloxanes, for example dimethylsilane, diphenylsilane, 1,1,3,3-tetra-methyldisiloxane.

Silanol terminated polydiorganosiloxanes of formula (7) which can be used in combination with the silicon hydride terminated polyimide to produce the silanol terminated polydiorganosiloxane-polyimide copolymer of formula (6) preferably have a viscosity in the range of from about 10 to 400,000 centipoise and preferably from about 1000 to about 250,000 centipoise when measured at about 25° C. These silanol terminated fluids can be made by treating a higher molecular weight organopolysiloxane, for example, a dimethylpolysiloxane with water in the presence of a mineral acid or base catalyst. Hydrolysis of diorganohalosilane, for example, dimethyldichlorosilane, diphenyldichlorosilane, methylvinyldichlorosilane, methylfluoropropyldichlorosilane, methylcyanoethyldichlorosilane, or mixtures thereof can produce low molecular weight polymer. Equilibration thereafter can provide for higher molecular weight organopolysiloxane. Organopolysiloxane also can be treated with steam under pressure or other procedures described in U.S. Pat. No. 2,607,792, and U.K. Pat. No. 835,790.

Some of the condensation catalysts which can be used to make the silanol terminated polydiorganosiloxane polyimide copolymer of formula (6) are platinum catalysts, for example, platinum complexes of unsaturated siloxanes, as shown by Karstedt U.S. Pat. No. 3,775,442, Ashby U.S. Pat. Nos. 3,159,601, and 3,159,662 and Lamoreaux U.S. Pat. No. 3,220,972, assigned to the same assignee as the present invention. An effective amount of a platinum, catalyst is about $10^{-4}\%$ to 0.1% by weight of platinum, based on the weight of curable hydrosilation mixture.

Various fillers and pigments can be incorporated into the room temperature vulcanizable compositions of the present invention. For example, there can be used, titanium dioxide, zirconium silicate, silica aerogel, iron oxide, diatomaceous earth, fumed silica, carbon black, precipitated silica, glass fibers, polyvinyl chloride, ground quartz, calcium carbonate, etc. The amounts of filler used can obviously be varied within wide limits in accordance with the intended use. For example, in some sealant applications, the curable compositions of the present invention can be used free of filler. In other applications, such as the employment of the curable compositions for making binding material on a weight basis, as much as 700 parts or more of filler, per 100 parts of polydiorganosiloxane-polyimide copolymers can be employed. In such applications, the filler can consist of a major amount of extending materials, such as ground quartz, polyvinyl chloride, or mixtures thereof, preferably having an average particle size in the range of from about 1 to 10 microns.

The condensation vulcanizable compositions of the present invention also can be employed as construction sealants and caulking compounds. The exact amount of filler, therefore, will depend upon such factors as the application for which the organopolysiloxane composition is intended, the type of filler utilized (that is, the density of the filler and its particle size). Preferably, a proportion of from 5 to 300 parts of filler, which can include up to about 35 parts of reinforcing filler, such as fumed silica filler, per 100 parts of silanol terminated organopolysiloxane is utilized.

The silicon hydride terminated polyimide of formula (5) can be used as an adhesion promoter in room temperature vulcanizable organopolysiloxane compositions. The silanol-terminated polydiorganosiloxane polyimide copolymer of formula (6) can be used as an impact modifier in room temperature vulcanizable organopolysiloxane compositions as previously discussed.

In the practice of the present invention, the condensation vulcanizable polydiorganosiloxane-polyimide copolymer compositions can be made by mixing the curing agent, condensation catalyst and optionally cross-linking agent with the silanol terminated polydiorganosiloxane-polyimide copolymer of formula (60, referred to hereinafter as the "silanol polyimide copolymer".

There can be utilized in the condensation vulcanizable compositions of the present invention, an effective amount of the curing agent as previously defined which may vary depending upon whether a one-package or two-package is desired, or whether the curing agent utilized will generate an acidic or substantially neutral by-product. For example, in instances where an acyloxy curing agent is used, such as methyltriacetoxysilane, effective results can be achieved if from 0.002 to 10 parts of methyltriacetoxysilane per 100 parts of the silanol-polyimide copolymer is used. A curing agent, such as shown by formula (8), can be utilized at from 0.002 to 10 parts of curing agent per 100 parts of the silanol-polyimide copolymer. A cross-linking agent, as shown by formula (9) also can be used in combination with the curing agent of formula (8) in proportions of from 0 to 10 parts of cross-linking agent per 100 parts of the silanol-polyimide copolymer. Condensation catalyst also can be used in the proportions as previously defined.

As taught previously, the above-described condensation vulcanizable compositions also can be combined with various fillers, pigments and extenders which can be optionally incorporated into the silicone-polyimide copolymer prior to, along with, or after the incorporation of the curing agent, condensation catalyst, etc.

The synthesis of the norbornene terminated polyimide of formula (3) can be accomplished by conventional procedures, utilizing substantially equal molar amounts of the organic diamine dianhydride along with an effective amount of the chain-stopping norbornene anhydride which can be utilized in an amount sufficient to produce the polyimide at a desired molecular weight. During the polymerization of the norbornene terminated polyimide, there can be utilized organic solvents, for example, orthodichlorobenzene, and temperature in the range of from 140° C. to 200° C. can be employed. Reaction can be conducted in an inert atmosphere, for example, under nitrogen to minimize undesirable side reactions. Reaction times can vary from 30 minutes or less to 3 hours, depending upon the nature of the reactants, the molecular weight of the polyimide desired, etc.

The silicon hydride terminated polyimide of formula (5) can be synthesized by effecting reaction between norbornene terminated polyimide of formula (3) and an appropriate silicon hydride of formula (4), such as a dihydrogen silane, dihydrogen disiloxane, in the presence of an effective amount of a platinum catalyst. An effective amount of platinum catalyst is from about $10^{-6}$ parts to $10^{-3}$ parts of platinum, per part of the hydrosilation mixture consisting of the norbornene terminated polyimide, silicon hydride and an inert organic solvent which can be utilized in an amount sufficient to produce a mixture having from 10% to 50% by weight of solids. Suitable inert organic solvents which can be used are, for example, chlorobenzene and orthodichlorobenzene. Hydrosilation is preferably conducted under substantially anhydrous conditions at a temperature in the range of from 15° C. to 90° C.

The preparation of the silanol-polyimide can be achieved by effecting reaction between the silicon hydride terminated polyimide of formula (5) and the silanol-terminated polydiorganosiloxane of formula (7) at a temperature in the range of from 15° C. to 150° C. in the presence of an effective amount of copolymerization catalyst. Suitable copolymerization catalysts include for example, amine, alkali metal fluoride, colloidal nickel, zinc chloride, platinum, or rhodium complexes, dibutyltindiacetate, with or without an aprotic solvent to facilitate reaction, such as dichloromethane, chlorobenzene, orthodichlorobenzene, etc, depending upon the mutual solubility of the reactants.

The condensation vulcanizable silicon-polyimide compositions also can be blended with silanol-terminated polydiorganosiloxane of formula (7) as described above. The blending can be accomplished under substantially anhydrous conditions at a temperature in the range of from about 15° C. to about 200° C. or higher. The resulting cured silicon-polyimide copolymers can be utilized in a variety of applications requiring high strength, high performance, temperature resistant elastomers.

In order that those skilled in the art will be better able to practice the invention, the following examples are given by way of illustration and not by way of limitation. All parts are by weight.

EXAMPLE 1

There was added a mixture of 13.68 grams of 5-norbornene-2,3-dicarboxylic anhydride and 43.33 grams of 2,2-bis[4-(3,4-dicarboxyphenoxy)phenyl]propane dianhydride over a period of 10 minutes under nitrogen to a solution of 13.51 grams of meta-phenylene diamine and 100 ml o-dichlorobenzene. The resulting solution was heated to reflux for 2 hours while water was continuously removed azeotropically. The resulting solution was poured into 400 ml of methanol and stirred vigorously. A product was precipitated which was filtered, washed with methanol and dried. Based on method of preparation the product had the following formula, was a silicon hydride terminated polyetherimide having the formula,

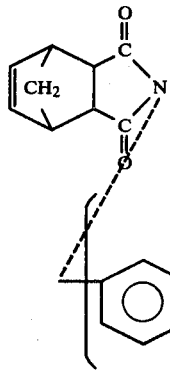

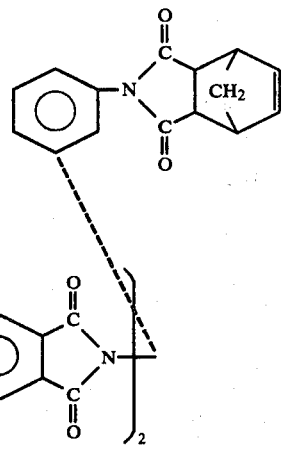

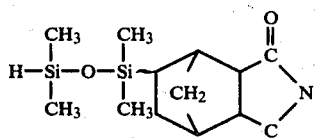

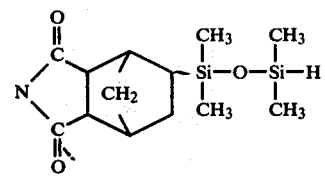

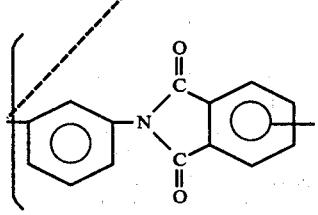

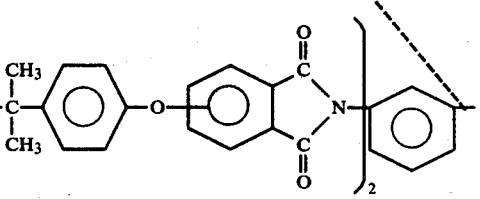

There was obtained 64.8 grams of the above norbornene terminated polyetherimide, which represented a yield of 97%.

There was added under a nitrogen atmosphere 5 drops of a 5% platinum catalyst prepared in accordance with Karstedt U.S. Pat. No. 3,775,442 to a mixture of 22.0 grams of the above norbornene terminated polyetherimide, 4.0 gram of 1,1,3,3-tetramethyldisiloxane and 40 ml of dry chlorobenzene. The solution was stirred and heated to 70° C. for about 12 hours. Carbon black was added to the resulting mixture at room temperature and the solution was stirred 30 minutes. The mixture was then filtered and the filtrate was poured into 200 ml of dry diethyl ether with vigorous stirring. There was obtained a precipitate which was filtered, washed with diethyl ether and dried. Based on method of preparation, the precipitate which was obtained at a 98% yield, The identity of the product was further confirmed by NMR and IR analysis.

There was added 1 drop of a 5% solution of the above Karstedt catalyst under nitrogen to a mixture of 5.58 gm of the above-described silicon hydride terminated polyetherimide, 34.02 gm of a silanol terminated polydimethylsiloxane having 0.31 weight percent of silanol in 30 ml of dry dichloromethane. The resulting solution was heated to 80° C. for 3 hours. Infrared analysis showed that silicon hydride was absent from the resulting mixture. There was obtained an opaque residue having a viscosity of 146,200 centipoise when the solvent was evaporated from the mixture. Based on method of preparation, the opaque residue was a silanol terminated polydimethylsiloxane-polyetherimide block copolymer having the formula,

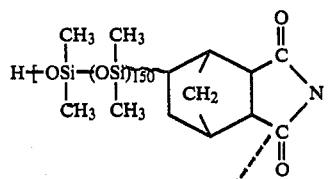 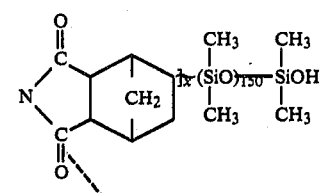

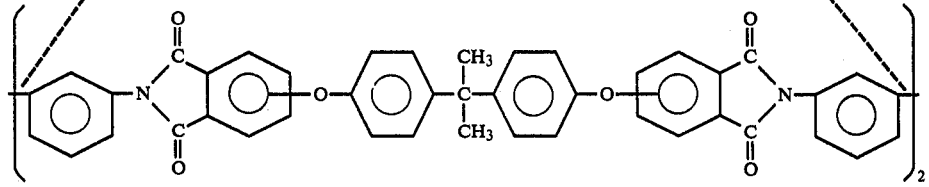

where x is an integer greater than 2.

There was mixed under substantially anhydrous conditions to the above silanol terminated silicon-polyetherimide copolymer, 1.0 gram mole of methyltrimethoxysilane followed by the addition of 0.1 gm of dibutyltindiacetate and 0.3 gm of dibutylamine. The resulting mixture was allowed to stand for 1 week under a 58% humidity environment. There was obtained a tack-free cured block polymer having a tensile strength (psi) of 146 and an elongation (%) of 630.

The above procedure was repeated, except that a silanol terminated polydimethylsiloxane having a viscosity of 146,000 centipoise at 25° C. was substituted for the silanol terminated polydimethylsiloxane-polyetherimide block copolymer. There was obtained a cured product having a tensile strength (psi) of 49 and an elongation (%) of 300.

EXAMPLE 2

A mixture of methylene dianiline (9.91 gm, 0.05 mol), 5-norbornene 2,3-dicarboxylic acid monomethyl ester (19.62 gm, 01 mol), and dry methanol (100 ml) was refluxed for 2 hours under $N_2$. After removal of the solvent, the residue was heated to 150° C. for 2 hours under $N_2$ in an oven. There was obtained a white solid which was dissolved in $CH_2Cl_2$ and poured into methanol (400 ml) and stirred vigorously. Based on method of preparation, there was obtained a bis(norbornene imide) which was filtered, washed with methanol and dried. There was obtained a 98% yield of bisimide having the formula,

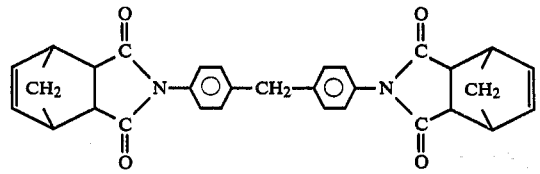

There was added under nitrogen to a solution of 100 ml of dry chlorobenzene and 5.26 g ($1 \times 10^{-2}$ of the above bis(norbornene imide), 4 g ($3 \times 10^{-2}$ mol) of 1,1,3,3-tetramethyldisiloxane and 5 drops of 5% of a Pt catalyst shown by Karstedt U.S. Pat. No. 3,715,334. The resulting solution was heated to 60°–80° C. overnight. After removal of excess 1,1,3,3-tetramethyldisiloxane, carbon black was added to the solution. The mixture was stirred for 1 hour and then filtered. Based on method of preparation, there was obtained a silicon hydride terminated bisimide of the formula,

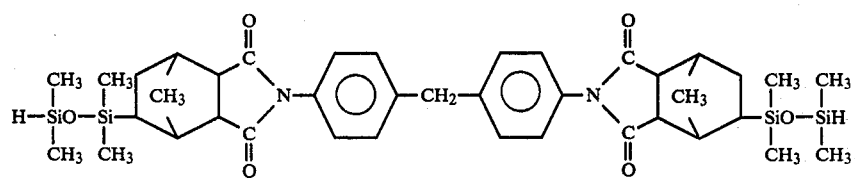

The above silicone hydride terminated bisimide was mixed with silanol terminated polydimethylsiloxane (15.23 gm, 2.6 OH wt %) and Cl Rh (PPh₃) (3 mg) and then heated to 80° C. for 2 hours. Removal of the solvent gave clear high viscous residue. Based on method of preparation the residue was a silanol terminated bisimide siloxane of the formula,

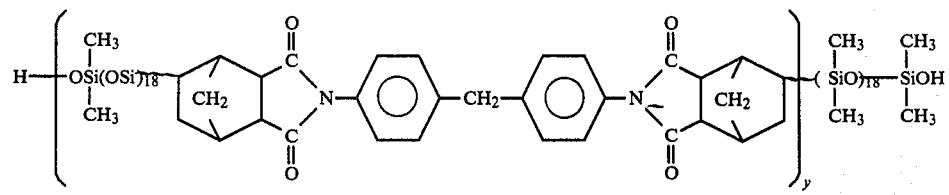

where y is an integer greater than 10. The residue was subsequently mixed with methyltriacetoxysilane (0.1 gm) followed by addition of $Bu_2Sn(OAc)_2$. The resulting mixture was allowed to stand for 1 week under 58% humidity environment. The cured material was transparent rubber with substantially improved toughness and elongation.

EXAMPLE 3

A norbornene terminated bisimide was prepared by dissolving 174 grams of isophorone diamine and 328 grams of norborndicarboxylic anhydride in 1800 ml of N-methylpyrrolidone and 600 ml of toluene. The reaction mixture was heated to remove water over a period of 12 hours. The mixture was then heated to effect a partial removal of toluene and some N-methylpyrrolidone. The residue was poured into 40% isopropanol. There was obtained a beige solid which was collected by filtration and dried.

A solution of 46.2 grams of the above isophorone norbornene terminated diimide and 20 ppm of platinum catalyst and 200 ml of chlorobenzene was treated with 32.6 parts of tetramethyldisiloxane at 80°–100° C. for 6 hours to produce an isophorone diimidedihydrosiloxane. There was condensed about 73 parts of the diimidohydrosiloxane with a silanol terminated polydimethylsiloxane fluid having an average of about 3 chemically combined siloxy units in about a 1:1 and 1:2 mole ratio in the presence of a platinum catalyst at a temperature of 50°–60° C. to produce silanol terminated polydiorganosiloxane polyimide copolymer within the scope of formula (6).

A condensation curable mixture was prepared under anhydrous conditions consisting of 20 grams of silanol terminated polydimethylsiloxane-polyimide copolymer made from a mixture having a ratio of 2 moles of the silanol terminated dimethylsiloxane with 1 mole of the diimidohydrosiloxane, 100 grams of a silanol terminated polydimethylsiloxane having a viscosity of 120–180,000 centipoise, 4 grams of methyltrimethoxysilane, 0.5 gram of dihexylamine and 0.3 gram of dibutyltindiacetate.

The above RTV composition was exposed to air and it cured within 10 to 16 minutes. Test slabs were prepared to determine hardness (Shore A), elongation (%) and tensile (psi). The following results were obtained:

| Hardness | 17 |
| Elongation | 372 |
| Tensile | 143 |

The above procedure was repeated, except that an RTV was prepared free of the silanol terminated polydiorganosiloxane polyimide copolymer of the present invention. The following results were obtained:

| Hardness | 9 |
| Elongation | 328 |
| Tensile | 53 |

The above results show that the silanol terminated polydimethylsiloxane polyimide copolymer imparts improved physical properties to conventional room temperature vulcanizable organopolysiloxane compositions.

EXAMPLE 4

The procedure of Example 3 was repeated, except that the silanol terminated polydimethylsiloxane-polyimide copolymer used was prepared from the mixture of the silicon hydride terminated diimide and silanol terminated polydimethylsiloxane in a 1:1 mole ratio. This silanol terminated polydimethylsiloxane polyimide was further blended with the ingredients of the room temperature vulcanizable composition of Example 3, except that there was utilized a silanol terminated polydimethylsiloxane having a viscosity of 20–50,000 centipoise. In addition, there was added octamethylcyclotetrasiloxane and disilazane treated fumed silica to the mixture in a proportion of 5% and 10% by weight, based on the weight of the total mixture. The various mixtures were allowed to cure under atmospheric conditions as described in Example 3 and the following results were obtained, where "5% Filler" and "10% Filler" means the aforementioned filled formulations and Shore A, Elongation and Tensile are as previously defined:

|  | 5% Filler | 10% Filler |
| --- | --- | --- |
| Hardness | 32 | 35 |
| Elongation | 253 | 269 |
| Tensile | 331 | 255 |

The above procedure was repeated, except that the silanol terminated polydimethylsiloxane-polyimide copolymer was not used in the formulation. The following results were obtained:

|  | 5% Filler | 10% Filler |
| --- | --- | --- |
| Hardness | 22 | 27 |
| Elongation | 288 | 251 |
| Tensile | 168 | 231 |

The above results show that a significant increase in toughness is imparted to cured room temperature vulcanizable organopolysiloxane compositions as a result of incorporation of the silanol terminated polydimethylsiloxane-polyimide copolymer of the present invention.

Although the above examples are directed to only a few of the very many condensation vulcanizable silicone-polyimide copolymers which include room temperature vulcanizable and low temperature vulcanizable compositions within the scope of the present invention, it should be understood that the present invention is directed to a much broader variety of condensation vulcanizable compositions based on the use of a silanol terminated polydiorganosiloxane-polyimide copolymer in combination with a curing agent as shown by formula (8) and optionally with a cross-linking agent as shown by formula (9) in further combination with a condensation catalyst. In addition, the present invention is also directed to the silicon hydride terminated polyimide of formula (5) and silanol-polyimide copolymer of formula (6) which are materials useful in making condensation vulcanizable compositions convertible to high strength silicon-polyimide copolymers in the cured state.

What I claim as new and desire to secure by Letters Patent of the United States is:

1. Condensation vulcanizable compositions comprising a silanol terminated polydiorganosiloxane-polyimide copolymer.

2. Condensation vulcanizable compositions comprising by weight
   (A) 100 parts of a silanol terminated polydiorganosiloxane-polyimide copolymer,
   (B) 0.002 to 10 parts of a curing agent,
   (C) 0 to 5 parts of a condensation catalyst and
   (D) 0 to 3000 parts of a silanol-terminated polydiorganosiloxane.

3. A condensation vulcanizable composition in accordance with claim 1, which is curable at room temperature.

4. A condensation vulcanizable composition in accordance with claim 1, which is moisture curable.

5. A room temperature vulcanizable composition in accordance with claim 1, where the curing agent is an alkoxy silane having the formula, alkylcyano radicals, or $C_{(7-13)}$ aralkyl radical, X is a hydrolyzable leaving group selected from the group consisting of acyloxy, amido, amino, carbamato, enoxy, halo, imidato, isocyanato, ketoximato, oximato, thioisocyanato and ureido radicals and a is equal to 0 or 4 inclusive, b is a whole number equal to 0 or 1 and the sum of a+b is equal to from 0 to 4 inclusive.

6. A room temperature vulcanizable composition in accordance with claim 1, where the curing agent is trimethoxy-N-methylacetamide silane.

7. A room temperature vulcanizable composition in accordance with claim 1, where the curing agent is methyltriacetoxysilane.

8. A silicon hydride terminated polyimide of the formula,

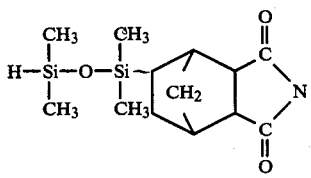
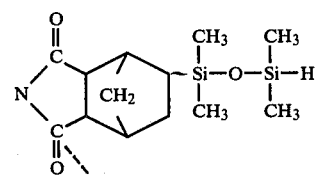
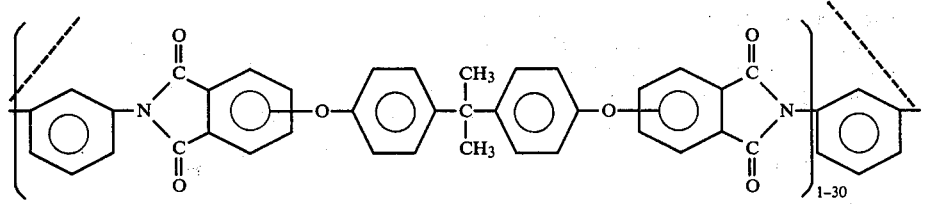

9. A silanol terminated polydimethylsiloxane-polyimide copolymer of the formula

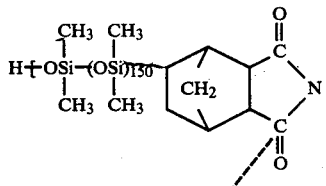
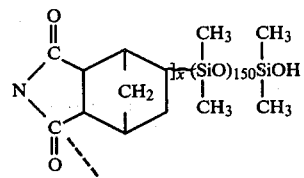
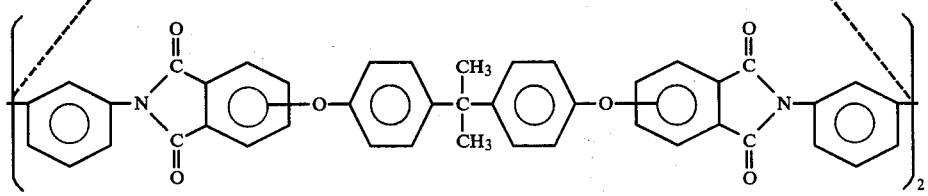

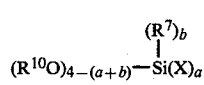

where $R^7$ is selected from the class consisting of $C_{(1-13)}$ monovalent hydrocarbon radicals and substituted $C_{(1-13)}$ monovalent hydrocarbon radicals, $R^{10}$ is a $C_{(1-8)}$ aliphatic organic radical selected from the group consisting of alkyl, alkylether, alkylester, alkylketone, and where x is an integer greater than 2.

10. A condensation vulcanizable composition in accordance with claim 1, containing methyltrimethoxysilane.

11. A silanol or silicon hydride terminated polydiorganosiloxane-polyimide copolymer comprising by weight from 1 to 99% of polyimide blocks of the formula,

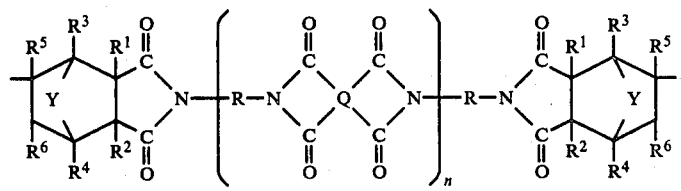

chemically combined with from 99% to 1% of polydiorganosiloxane blocks of the formula,

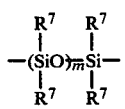

where R is a divalent radical selected from the class consisting of (a) aromatic hydrocarbon radicals having from 6–20 carbon atoms and halogenated aromatic hydrocarbon radicals having from 6–20 carbon atoms, (b) alkylene radicals having from 2–20 carbon atoms and cycloalkylene radicals having from 2–20 carbon atoms, (c) $C_{(2-8)}$ alkylene terminated polydiorganosiloxane, and (d) radicals included by the general formula,

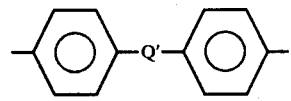

Q' is a member selected from the class consisting of

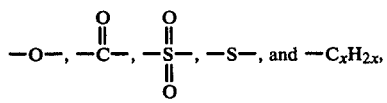

x is a whole number from 1 to 5 inclusive, Q is a tetravalent radical selected from

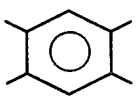

and

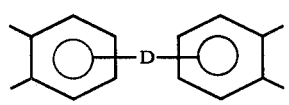

where D is a member selected from

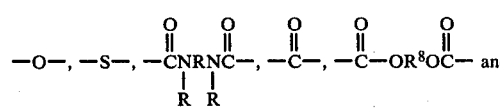

and $R^8$ is a divalent radical selected from

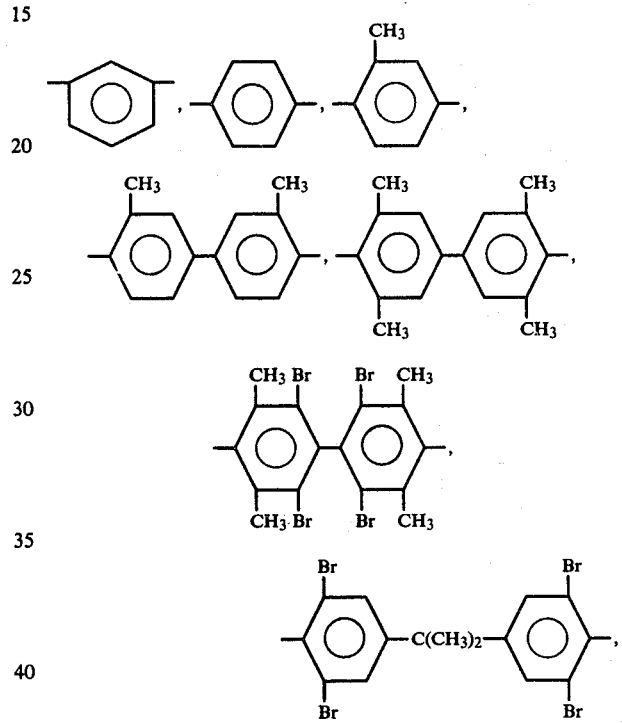

and divalent organic radicals of the general formula,

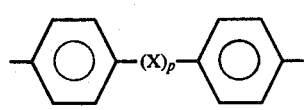

X is a member selected from the class consisting of divalent radicals of the formula,

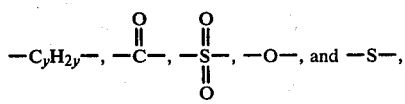

y is an integer from 1 to 5, $R^1$–$R^6$ are selected from hydrogen and $C_{(1-8)}$ alkyl radicals, $R^7$ is selected from the class consisting of $C_{(1-13)}$ monovalent hydrocarbon radicals and substituted $C_{(1-13)}$ monovalent hydrocarbon radicals, Y is a divalent radical selected from —O— and —C($R^1$)$_2$—, n is an integer equal to 0–200 inclusive, m is an integer equal to 1–2000 inclusive and p is equal to 0 or 1.

12. A silicon hydride terminated polyimide having the formula,

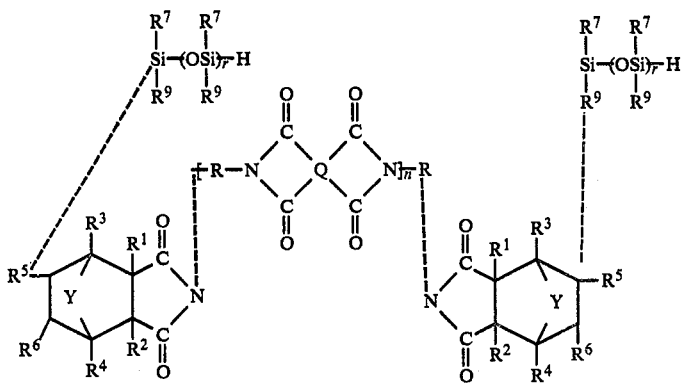

where R is a divalent radical selected from the class consisting of (a) aromatic hydrocarbon radicals having from 6-20 carbon atoms and halogenated aromatic hydrocarbon aromatic hydrocarbon radicals having from 6-20 carbon atoms, (b) alkylene radicals having from 2-20 carbon atoms and cycloalkylene radicals having from 2-20 carbon atoms, (c) $C_{(2-8)}$ alkylene terminated polydiorganosiloxane, and (d) radicals included by the general formula,

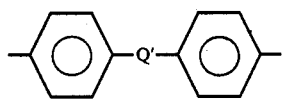

Q' is a member selected from the class consisting of

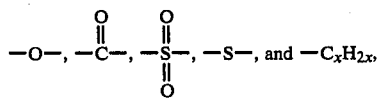

x is a whole number from 1 to 5 inclusive, Q is a tetravalent radical selected from

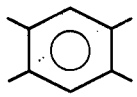

and

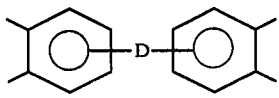

where D is a member selected from

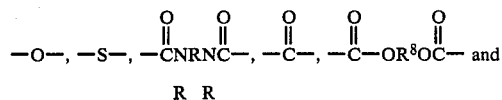

and $R^8$ is a divalent radical selected from

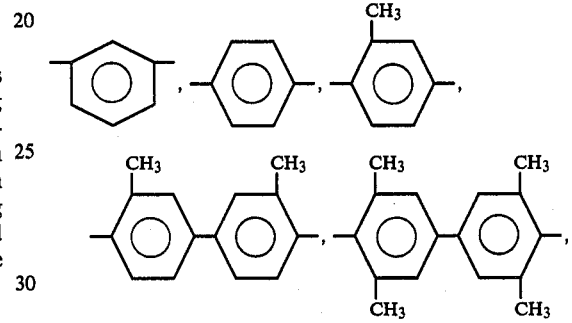

and divalent organic radicals of the general formula,

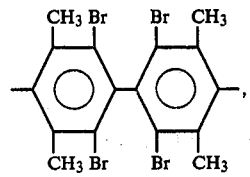

X is a member selected from the class consisting of divalent radicals of the formula,

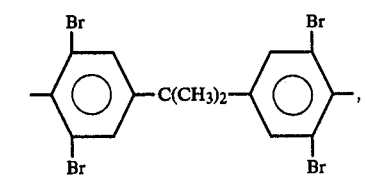

y is an integer from 1 to 5, $R^1$-$R^6$ are selected from hydrogen and $C_{(1-8)}$ alkyl radicals, $R^7$ is selected from the class consisting of $C_{(1-13)}$ monovalent hydrocarbon radicals and substituted $C_{(1-13)}$ monovalent hydrocarbon radicals, Y is a divalent radical selected from —O— and —C($R^1$)$_2$—, n is an integer equal to 0-200 inclusive, m is an integer equal to 1-2000 inclusive and p is equal to 0 or 1.

13. A silanol terminated polyimide having the formula,

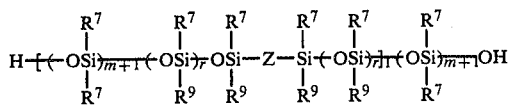

where Z is a divalent group shown by the formula,

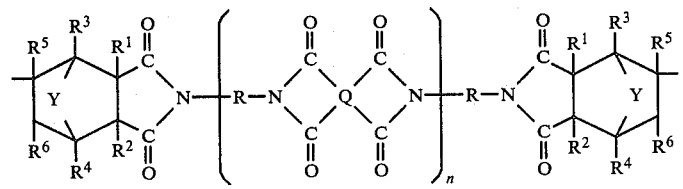

R is a divalent radical selected from the class consisting of (a) aromatic hydrocarbon radicals having from 6-20 carbon atoms and halogenated aromatic hydrocarbon radicals having from 6-20 carbon atoms, (b) alkylene radicals having from 2-20 carbon atoms and cycloalkylene radicals having from 2-20 carbon atoms, (c) $C_{(2-8)}$ alkylene terminated polydiorganosiloxane, and (d) radicals included by the general formula,

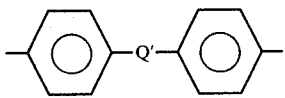

Q' is a member selected from the class consisting of

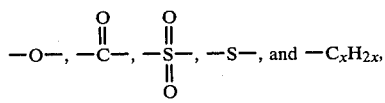

x is a whole number from 1 to 5 inclusive, Q is a tetravalent radical selected from

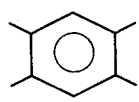

and

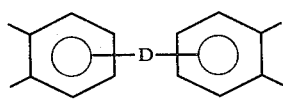

where D is a member selected from

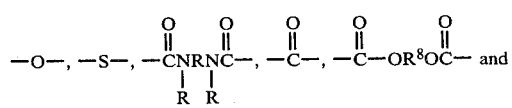

and $R^8$ is a divalent radical selected from

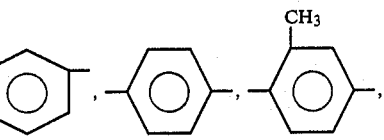

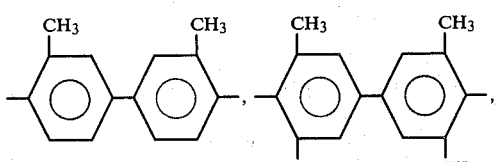

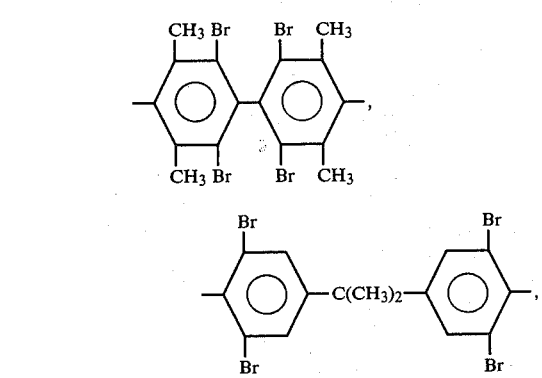

and divalent organic radicals of the general formula,

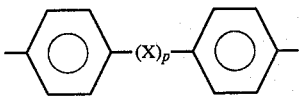

X is a member selected from the class consisting of divalent radicals of the formula,

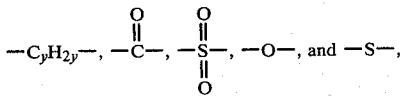

y is an integer from 1 to 5, $R^1$-$R^6$ are selected from hydrogen and $C_{(1-8)}$ alkyl radicals, $R^7$ is selected from the class consisting of $C_{(1-13)}$ monovalent hydrocarbon radicals and substituted $C_{(1-13)}$ monovalent hydrocarbon radicals, $R^9$ is selected from hydrogen and $R^7$, Y is a divalent radical selected from —O— and —C($R^1$)$_2$—, n is an integer equal to 0-200 inclusive, p is equal to 0 or 1, r is a whole number equal to 0 or 1, m is an integer equal to 1-2000 inclusive and l is an integer having a value of from about 1 to $10^4$ inclusive.

* * * * *